United States Patent
Kurien et al.

(10) Patent No.: US 11,238,708 B1
(45) Date of Patent: Feb. 1, 2022

(54) DETECTING AND MANAGING AUDIENCE ENGAGEMENT

(71) Applicant: International Business Machines Corporation, Armonk, NY (US)

(72) Inventors: Toby Kurien, Midrand (ZA); Richard Allen Young, Johannesburg (ZA); Komminist Weldemariam, Ottawa (CA)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 16/925,725

(22) Filed: Jul. 10, 2020

(51) Int. Cl.
  *G08B 5/22* (2006.01)
  *G06F 3/01* (2006.01)
  *A61B 5/11* (2006.01)

(52) U.S. Cl.
  CPC .............. *G08B 5/221* (2013.01); *G06F 3/011* (2013.01); *A61B 5/1116* (2013.01)

(58) Field of Classification Search
  CPC ........ G08B 5/221; G06F 3/011; A61B 5/1116
  See application file for complete search history.

(56) References Cited

U.S. PATENT DOCUMENTS

| | | | |
|---|---|---|---|
| 8,932,236 B1 | 1/2015 | McKeon | |
| 9,041,766 B1 | 5/2015 | Gates | |
| 9,525,952 B2 | 12/2016 | Bowden | |
| 9,785,228 B2 * | 10/2017 | Schwesinger | ........... G06F 3/005 |
| 9,795,322 B1 | 10/2017 | Karunaratne | |
| 10,068,490 B2 | 9/2018 | Hibbs | |
| 10,783,261 B1 * | 9/2020 | Gu | .......................... H04L 63/102 |
| 2010/0257268 A1 * | 10/2010 | Landry | .................. G09B 23/28 709/225 |
| 2011/0295392 A1 * | 12/2011 | Cunnington | ............. H04N 7/15 700/90 |

(Continued)

OTHER PUBLICATIONS

"System and Method to Enable Attentive Learning in Classroom using Personalized Warning and Intervention", An IP.com Prior Art Database Technical Disclosure, 3 pps.,IP.com No. IPCOM000240060D IP.com Electronic Publication Date: Dec. 29, 2014, <https://priorart.ip.com/IPCOM/000240060Dn>.

(Continued)

*Primary Examiner* — Ryan W Sherwin
(74) *Attorney, Agent, or Firm* — Alexander G. Jochym

(57) ABSTRACT

Aspects of the present invention disclose a method, computer program product, and system for determining engagement levels of an audience and providing associated recommendations to a presenter. The method includes one or more processors receiving sensor data from sensors located in an audience area during a presentation. The method further includes one or more processors determining an engagement level for a first individual in the audience area utilizing sensor data from sensors associated with the first individual. The method further includes one or more processors determining whether the determined engagement level for the first individual indicates that the first individual is not engaged with the presentation. In response to determining that the determined engagement level of the first individual indicates that the first individual is not engaged with the presentation, the method further includes one or more processors determining recommendations to increase engagement of the first individual.

20 Claims, 3 Drawing Sheets

(56) References Cited

U.S. PATENT DOCUMENTS

| | | | |
|---|---|---|---|
| 2014/0046144 A1* | 2/2014 | Jayaraman | G06K 9/0053 600/301 |
| 2014/0205990 A1 | 7/2014 | Wellman | |
| 2017/0035823 A1 | 2/2017 | Sheu | |
| 2017/0039876 A1 | 2/2017 | Alyuz Civitci | |
| 2017/0070305 A1 | 3/2017 | Bowden | |
| 2017/0279957 A1* | 9/2017 | Abramson et al. | G06F 21/36 |
| 2017/0295404 A1* | 10/2017 | Meredith | H04H 60/33 |
| 2017/0352285 A1* | 12/2017 | Selen | G09B 5/14 |
| 2018/0151082 A1* | 5/2018 | Duggan | G09B 7/10 |
| 2018/0213079 A1* | 7/2018 | Kenjalkar | H04M 1/72463 |
| 2018/0293905 A1 | 10/2018 | Benz | |

OTHER PUBLICATIONS

D'Mello et al., "Advanced, Analytic, Automated (AAA) Measurement of Engagement During Learning", (2017) Advanced, Analytic, Automated (AAA) Measurement of Engagement During Learning, Educational Psychologist, DOI: 10.1080/00461520.2017.1281747, 21 pps., <https://www.ncbi.nlm.nih.gov/pmc/articles/PMC5640167/>.

D'Mello et al., "Automatic Detection of Learner's Affect from Gross Body Language", This article was downloaded by [University of California, San Diego] on: Jun. 4, 2015, Publisher: Taylor & Francis, Applied Artificial Intelligence: An International Journal, 29 pps., <https://www.semanticscholar.org/paper/Automatic-Detection-of-Learner's-Affect-from-Gross-D'Mello-Graesser/52b8251589f20359afd9ba3ca129ad9a211f1123>.

Mota et al., "Automated Posture Analysis for Detecting Learner's Interest Level", Proceedings of the 2003 Conference on Computer Vision and Pattern Recognition Workshop (CVPRW'03) 1063-6919/03, © 2003 IEEE, 6 pps., <https://ieeexplore.ieee.org/document/4624309>.

Zaletelj et al., "Predicting students' attention in the classroom from Kinect facial and body features", Zaletelj and Košir EURASIP Journal on Image and Video Processing (2017) 2017:80, DOI 10.1186/s13640-017-0228-8, 12 pps., <https://link.springer.com/article/10.1186/s13640-017-0228-8>.

* cited by examiner

DETECTING AND MANAGING AUDIENCE ENGAGEMENT

BACKGROUND OF THE INVENTION

The present invention relates generally to the field of data analytics, and more particularly to determining audience engagement information.

Capacitive sensing (sometimes capacitance sensing) is a technology, based on capacitive coupling, that can detect and measure anything that is conductive or has a dielectric different from air. Many types of sensors use capacitive sensing, including sensors to detect and measure proximity, pressure, position and displacement, force, humidity, fluid level, and acceleration. Digital audio players, mobile phones, and tablet computers use capacitive sensing touchscreens as input devices. Capacitive sensors can also replace mechanical buttons. A capacitive touchscreen typically includes a capacitive touch sensor along with at least two complementary metal-oxide-semiconductor (CMOS) integrated circuit (IC) chips, an application-specific integrated circuit (ASIC) controller, and a digital signal processor (DSP). Capacitive sensing is commonly used for mobile multi-touch displays.

An accelerometer is a tool that measures proper acceleration. Accelerometers have many uses in industry and science. Highly sensitive accelerometers are used in inertial navigation systems for aircraft. Vibration in rotating machines is monitored by accelerometers. Accelerometers are also used in tablet computers and digital cameras (e.g., so that images on screens are always displayed upright, to detect movement, etc.).

SUMMARY

Aspects of the present invention disclose a method, computer program product, and system for determining engagement levels of an audience and providing associated recommendations to a presenter. The method includes one or more processors receiving sensor data from a plurality of sensors located in an audience area during a presentation. The method further includes one or more processors determining an engagement level for a first individual in the audience area utilizing sensor data from sensors associated with the first individual. The method further includes one or more processors determining whether the determined engagement level for the first individual indicates that the first individual is not engaged with the presentation. In response to determining that the determined engagement level of the first individual indicates that the first individual is not engaged with the presentation, the method further includes one or more processors determining one or more recommendations to increase engagement of the first individual.

DETAILED DESCRIPTION

Figure 1:
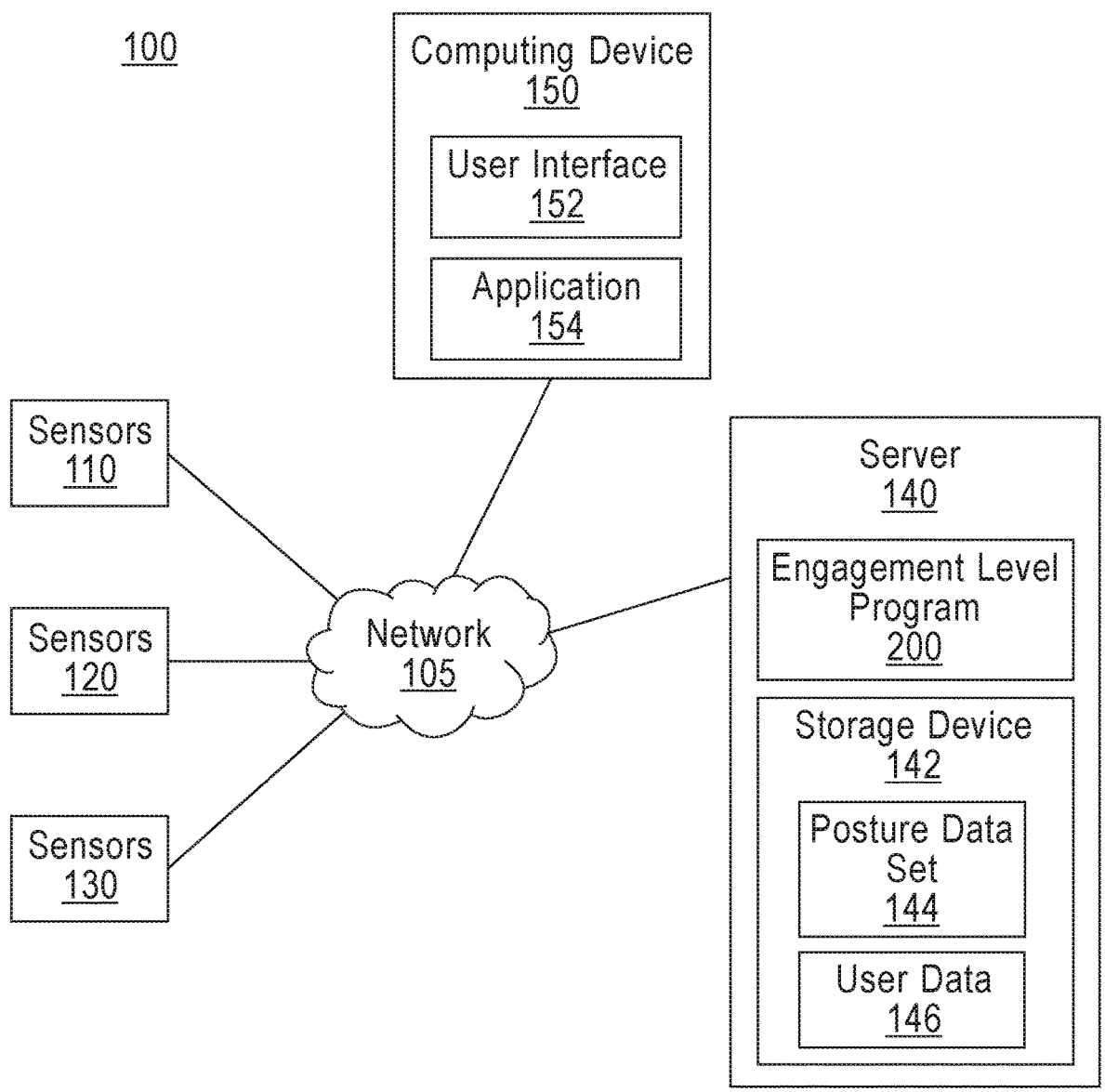
FIG. 1 is a functional block diagram of a data processing environment, in accordance with an embodiment of the present invention.

Embodiments of the present invention allow for determining an engagement level of an individual in an audience (e.g., a student in a classroom) by detecting and interpreting the posture and movements of the individual. Embodiments of the present invention utilize sensors located in the audience (e.g., capacitive touch sensors, accelerometers, etc.) to generate real-time posture information for audience members. Embodiments of the present invention further leverage an analytics model to determine the posture of audience members, based on the sensor data, and determine a corresponding engagement level based on the posture information. In response to determining that an engagement level of an individual indicates that the individual is not engaged, embodiments of the present invention can determine recommendations to increase engagement and send the recommendations (and corresponding data) to the presenter. Further embodiments of the present invention can store the results of performing the recommended actions (e.g., associated with the corresponding individual), for future use and analysis.

Embodiments of the present invention recognize that, in order for a presentation (e.g., a classroom lesson) to be effective, the audience needs to be engaged. Various factors can lead to audience disengagement, such as lesson content, individual (e.g., student) learning/content preferences, user skill/knowledge levels, external distractions (e.g., mobile device usage), etc. Further embodiments of the present invention recognize that, when an individual is disengaged, the individual can exhibit a posture that indicates the disengagement. For example, an audience member body posture can include various "tells" of disengagement, such as slouching, placing a hand and/or significant portion of a forearm on a desk, leaning forward with no contact with a desk (e.g., indicating mobile device usage below desk), foot tapping, etc. Embodiments of the presentation recognize that detecting and aggregating the "tells" over time can provide an accurate representation of engagement or disengagement of an audience member.

Accordingly, embodiments of the present invention can determine and map real-time signals from audience members (i.e., posture and body language data from capacitive sensors and accelerometers) and apply heuristics and learning algorithms to infer and model engagement and/or disengagement states of audience members. Further, embodiments of the present invention can determine and suggest personalized engagement actions, with the overall goal of improving the outcome of the presentation. In various embodiment, the "posture" of an individual can include both static posture information (e.g., how an individual is stated in a chair/desk) and motion posture information (e.g., an individual rocking back and forth in a chair, tapping a foot on the ground, etc.).

Implementation of embodiments of the invention may take a variety of forms, and exemplary implementation details are discussed subsequently with reference to the Figures.

The present invention will now be described in detail with reference to the Figures. FIG. 1 is a functional block diagram illustrating a distributed data processing environment, generally designated 100, in accordance with one embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

An embodiment of data processing environment 100 includes sensors 110, sensors 120, sensors 130, server 140, and computing device 150, all interconnected over network 105. In an example embodiment, server 140 is representative of a computing device (e.g., one or more management servers) that receives information from sensors 110, sensors 120, sensors 130, analyze the received information, and provide information to computing device 150. For example, server 140 receives sensor data from one or more of sensors 110, sensors 120, sensors 130 and server 140 (utilizing engagement level program 200) derives posture information and a corresponding engagement level for one or more users in an audience. In other embodiments, data processing environment 100 can include additional instances of computing devices and sensors (not shown) that can interface with server 140, in accordance with various embodiments of the present invention.

Network 105 can be, for example, a local area network (LAN), a telecommunications network, a wide area network (WAN), such as the Internet, or any combination of the three, and include wired, wireless, or fiber optic connections. In general, network 105 can be any combination of connections and protocols that will support communications between sensors 110, sensors. 120, sensors 130, server 140, and computing device 150, in accordance with embodiments of the present invention. In various embodiments, network 105 facilitates communication among a plurality of networked computing devices (e.g., sensors 110, sensors. 120, sensors 130, server 140, and computing device 150), corresponding users (e.g., users of computing device 150 or server 140, etc.), and corresponding management services (e.g., server 140).

In various embodiments of the present invention, sensors 110, sensors 120, and sensors 130 are respectively representative of a set of sensors that are located at defined locations in an environment (e.g., a presentation venue, a classroom, etc.). For example, respective instances of sensors 110, sensors 120, and sensors 130 are sensors that are embedded in chairs and desks in an audience area. In example embodiments, sensors 110 are embedded in a desk and chair utilized by a first individual (i.e., audience member, student, etc.), sensors 120 are embedded in a desk and chair utilized by a second individual, and sensors 130 are embedded in a table and one or more chairs utilized by one or more individuals seated at the table. In additional embodiments, data processing environment 100 can include additional instances of sensors, based on an amount of audience members and/or seating in an audience area.

Sensors 110, sensors 120, and sensors 130 can include a plurality of different types of sensors, in accordance with various embodiments of the present invention. In example embodiments, sensors 110, sensors 120, and sensors 130 include wireless sensors boards embedded in chairs and tables of an audience area, where the wireless sensor boards include capacitive touch sensors and accelerometers (movement) sensors. The accelerometers can operate to detect movements of a chair and/or desk, such as tapping on the desk, tapping a foot (which transfers oscillatory motion to the chair), tilting of the chair, etc. The capacitive sensors can operate similar to smartphone screen sensors. For example, the capacitive sensors can comprise a grid of wires meeting near a small air gap, which creates a field. When an individual touches the field (e.g., one centimeter or close proximity to the wires), the capacitance between the wires changes, which can be detected by a programmed microcontroller, and converted into a touch map.

Sensors 110, sensors 120, and sensors 130 can include a device that is a combination of the capacitive touch sensors and the accelerometers, along with a wireless communication module, embedded and/or mounted onto desk and chair surfaces. In example embodiments, each desk and chair in an audience area includes a respective instance of sensors 110, sensors 120, or sensors 130. Thus, an individual seated at a desk and chair in the audience area can generate a touch and motion map corresponding to the biomechanics of the individual, which embodiments of the present invention can utilize to estimate a posture of the seated individual. The sensor boards of sensors 110, sensors 120, and sensors 130 collect and relay data (via network 105) to server 140 for processing (e.g., utilizing engagement level program 200), in accordance with various embodiments of the present invention.

In another embodiment, the respective instances of sensors 110, sensors 120, and sensors 130 include logical groupings of sensors that represent one audience member. For example, sensors 110 is representative of a logical grouping of a plurality of sensors (e.g., arranged as a sensor board) that correspond to a specific student in a classroom. In this example, server 140 receives sensor data from sensors 110. The received sensor data include identifying information, which indicates that the data is from sensors 110, and also a corresponding location and/or indication of the specific student in the classroom. Accordingly, server 140 (utilizing engagement level program 200) can process the sensor data accurately, in accordance with embodiments of the present invention.

In an example embodiment, sensors 110, sensors 120, and sensors 130 are representative of standalone devices that include a capacitive touch sensor, an accelerometer, a battery, a microcontroller and/or microprocessor, and a wireless communication unit (e.g., for sending sensor data to server 140, via network 105). In another aspect, the standalone devices can include additional sensors, for collecting data in accordance with various embodiments of the present invention. In an example scenario, sensor 120 is a wireless sensor unit that is comprised of one or more capacitive touch sensors, one or more accelerometers, a battery, a microcontroller and/or microprocessor, and a wireless communication unit. In this example scenario, the wireless sensor unit includes a flat, flexible mat that includes a grid of wires that comprise the capacitive sensor, which is electronically coupled (E.g., via a cable) to a sensor unit that can include the one or more accelerometers, and other electrical components of the wireless sensor unit (mentioned above). In an example aspect, the sensor mat can easily attach and/or embed to a chair or desk (e.g., a 30-centimeter by 20-centimeter mat that can adhere to a chair back, chair cushion, or desk surface, etc.).

In various aspects of the present invention, individuals in an audience are made aware of presence and utilization of sensors 110, sensors 120, sensors 130, and other sensors (not shown) that are present in data processing environment 100. Accordingly, individuals in the audience can have the option to opt-out of sensor data collection, and/or define whether to opt-in or opt-out of certain categories of data collection. For example, an individual can opt-in for sensors to detect and gather all requested information, a subset of requested information, or no information. In addition, the audience area of data processing environment 100 can also include seating areas that do not include sensors, for available seating without data collection. In another embodiment, sensors 110, sensors 120, and sensors 130 can preserve privacy by not including video and audio sensor or recording equipment and functionality. In further embodiments, audience members can register preferences and data collection definitions with server 140, for storage in user data 146, in accordance with various embodiments of the present invention.

In example embodiments, server 140 can be a desktop computer, a computer server, or any other computer systems, known in the art. In certain embodiments, server 140 represents computer systems utilizing clustered computers and components (e.g., database server computers, application server computers, etc.) that act as a single pool of seamless resources when accessed by elements of data processing environment 100 (e.g., sensors 110, sensors 120, sensors 130, computing device 150, other devices not shown). In general, server 140 is representative of any electronic device or combination of electronic devices capable of executing computer readable program instructions. Server 140 may include components as depicted and described in further detail with respect to FIG. 3, in accordance with embodiments of the present invention.

Server 140 includes engagement level program 200 and storage device 142, which includes posture data set 144 and user data 146. In various embodiments of the present invention, server 140 operates as a computing system that receives data from sensors 110, sensors 120, and sensors 130 for utilization in determining engagement level information for individuals in an audience area. In an example embodiment, server 140 can be associated with the location of the audience area (e.g., a school, a presentation venue, etc.). In another embodiment, server 140 can be associated with a service provider that receives and analyzes sensor data, in accordance with various embodiments of the present invention.

In various embodiments, server 140 can operate as a central processing module that can wirelessly communicate with sensor boards located throughout a venue and audience area (i.e., sensors 110, sensors 120, and sensors 130). Server 140 (utilizing engagement level program 200) can convert signal readings from sensor boards to a corresponding engagement levels for respective audience members, and then provide/display the engagement level (and optionally an overall engagement level for the audience).

In example embodiments, engagement level program 200 determine engagement levels of an audience and provide associated recommendations to a presenter, in accordance with embodiments of the present invention. For example, engagement level program 200 can operate to determine the engagement level of learners within a classroom by detecting posture and body language information of the learners, utilizing non-invasive sensor boards, such as sensors 110, sensors 120, and sensors 130. In further aspects, engagement level program 200 can operate to execute an artificial intelligence (AI) algorithm that is trained to classify sensor signals (e.g., from desks and chairs) to determine respective engagement levels of audience members. Engagement level program 200 can also determine an overall engagement level (e.g., for a classroom) and display the overall engagement level to a presenter/teacher in near real-time, allowing the teacher/presenter to perform recommended actions intended to re-engage audience members as needed.

In additional embodiments, server 140 utilizes storage device 142 to store information associated with registered audience members and information for utilization in determining postures of audience members. For example, storage device 142 stores posture data set 144 and user data 146. Storage device 142 can be implemented with any type of storage device, for example, persistent storage 305, which is capable of storing data that may be accessed and utilized by server 140 and computing device 150, such as a database server, a hard disk drive, or a flash memory. In other embodiments, storage device 142 can represent multiple storage devices and collections of data within server 140.

In example embodiments, posture data set 144 is representative of a reference data set that server 140 can utilize to determine a user posture that corresponds to received sensor data. For example, posture data set 144 includes information that maps sensor data signals (e.g., from accelerometers and capacitive sensors of sensors 110, sensors 120, and sensors 130) to corresponding postures of audience members (i.e., a mapping of a combination of sensors signals to s slouching posture, etc.). In addition, posture data set 144 can include mapped relationships between posture information to corresponding engagement levels. For example, posture data can include a mapping that posture information of slouching in the chair and foot tapping maps to an engagement level of not engaged.

Embodiments of the present invention recognize that, when an individual is disengaged, the individual can exhibit a posture that indicates the disengagement. For example, an audience member body posture can include various "tells" of disengagement, such as slouching, placing a hand and/or significant portion of a forearm on a desk, leaning forward with no contact with a desk (e.g., indicating mobile device usage below desk), foot tapping, etc. Accordingly, posture data set 144 includes information that maps sensor data to corresponding various posture "tells" of disengagement.

In various embodiments, server 140 (or another entity/service) can generate posture data set 144 utilizing labelled posture training data. In example embodiments, a labelled training data set is gathered from capacitive sensors and accelerometers while students simulate engaged postures and disengaged postures, including the usage of mobile devices, during a lesson or presentation. Training data can be gathered as periodic snapshots of the current sensor state or as a vector of sensor states over a period of time. Further, a machine learning or deep learning model is trained on the training sensor data to classify a dataset as depicting wither engaged or disengaged behavior. In example embodiments, the AI model can be based on a human pose detection deep learning model. In additional embodiments, posture data set 144 can include the posture training data, and engagement level program 200 can leverage posture data set to determine a corresponding posture from received real-time sensor data, in accordance with embodiments of the present invention.

In another aspect, server 140 includes user data 146, which is representative of aggregated information associated with particular individuals in an audience (e.g., an audience of a presentation, learners in a classroom, etc.), in accordance with various embodiments of the present invention. In various embodiments of the present invention, a user (i.e., an audience member) can register with server 140 (e.g., utilizing a device associated with the user). For example, the user completes a registration process, provides information, and authorizes the collection and analysis (i.e., opts-in) of relevant data from sensors in an audience area (i.e., sensors 110, sensors 120, sensors 130, social media data, etc.). In additional embodiments, the user a user can opt-in or opt-out of certain categories of data collection from sensors, and/or analysis by server 140 (as discussed above).

Server 140 can store received definitions and preferences of an audience member in storage device 142 as a respective instance of user data 146 that corresponds to the audience member. For example, user data 146 can store user-preferred actions to increase engagement, user posture preference information, topics of interest, and other relevant information provided by the user (i.e., an audience member) and/or other users (i.e., administrator users, such as teachers or presenters).

In additional embodiments, user data 146 includes user profile data for users (i.e., audience members) and relevant historical data associated with the users. In example embodiments, user data 146 stores historical data collected from sensors and historical posture and engagement data derived by engagement level program 200. In additional example embodiments, user data 146 can store indications of actions that have successfully (and alternatively, unsuccessfully) increased engagement for respective audience members (in response to a recommendation by engagement level program 200).

In another aspect, server 140 can learn and use a particular context of a learner (i.e., an audience member), such as time of day, context generated from social media, context based on learned content of audience members, factors associated with engagement boost or decline, planned learning goals, etc. Server 140 can further store the learned contextual information associated with the learner a corresponding instance of user data 136. In additional embodiments, server 140 can create a unique signature model corresponding to individual audience members, based on analyzing posture and body language data observed over time periods, in combination with historical movement data (e.g., from the accelerometers). Server 140 can store the unique signature model as a component of user data 146, for utilization in distinguishing one audience member from another audience member. For example, server 140 can analyze and compare received sensor data from two users that are seated at a common table. In this example, server 140 can utilize respective stored signature models (in user data 146) for the two users to differentiate the users, and further identify respective user profiles of the two users at the common table.

In various embodiments of the present invention, computing device 150 may be a workstation, personal computer, personal digital assistant, mobile phone, or any other device capable of executing computer readable program instructions, in accordance with embodiments of the present invention. In general, computing device 150 is representative of any electronic device or combination of electronic devices capable of executing computer readable program instructions. Computing device 150 may include components as depicted and described in further detail with respect to FIG. 3, in accordance with embodiments of the present invention. In an example embodiment, computing device 150 is a personal workstation or mobile device associated with (e.g., registered to) a user that associated with server 140, in accordance with embodiments of the present invention. For example, computing device 150 is a computing device associated with a presenter (e.g., teacher) that is presenting to an audience (associated with sensors 110, sensors 120, and sensors 130), in accordance with various embodiments of the present invention.

Computing device 150 includes user interface 152 and application 154. User interface 152 is a program that provides an interface between a user of computing device 150 and a plurality of applications that reside on the device (e.g., application 154). A user interface, such as user interface 152, refers to the information (such as graphic, text, and sound) that a program presents to a user, and the control sequences the user employs to control the program. A variety of types of user interfaces exist. In one embodiment, user interface 152 is a graphical user interface. A graphical user interface (GUI) is a type of user interface that allows users to interact with electronic devices, such as a computer keyboard and mouse, through graphical icons and visual indicators, such as secondary notation, as opposed to text-based interfaces, typed command labels, or text navigation. In computing, GUIs were introduced in reaction to the perceived steep learning curve of command-line interfaces which require commands to be typed on the keyboard. The actions in GUIs are often performed through direct manipulation of the graphical elements. In another embodiment, user interface 152 is a script or application programming interface (API).

Application 154 can be representative of one or more applications (e.g., an application suite) that operate on computing device 150. In various example embodiments, application 154 can be an application that a user of computing device 150 utilizes to manage a presentation to an audience. In another example, application 154 is a client-side application associated with server 140 (e.g., and engagement level program 200) that a presenter can utilize to receive information and notifications, in accordance with various embodiments of the present invention.

For example, computing device 150, via application 154, can receive information from engagement level program 200 (e.g., engagement level information, real-time engagement data, recommendations of actions to increase engagement, etc.). In this example, a user of computing device 150 (e.g., a presenter) can provide feedback (e.g., via user interface 152) in response to received data from engagement level program 200, based on observed audience actions, etc. Server 140 (e.g., via engagement level program 200) can analyze the received feedback from a presenter and update user data 146 accordingly, in accordance with embodiments of the present invention.

In other embodiments, data processing environment 100 can include additional computing devices (not shown), such as computing devices associated with audience members, and other users, etc. In further embodiments, server 140 can operate engagement level program in a variety of types of environments (e.g., a boardroom, auditorium, online meetings, etc.) to provide feedback and recommendations to a presenter in an effort to increase engagement of audience members to the topic being discussed.

Figure 2:
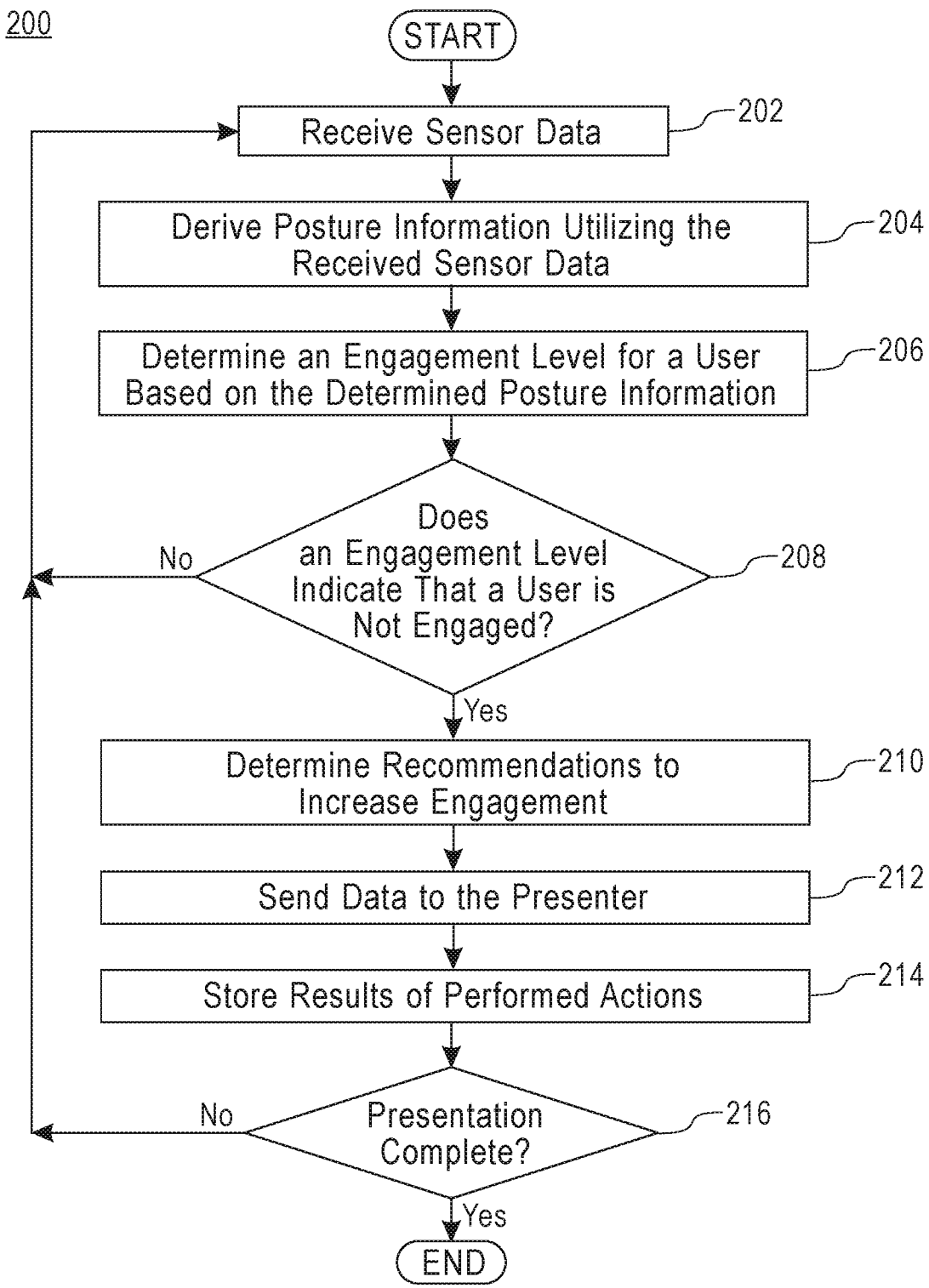
FIG. 2 is a flowchart depicting operational steps of a program for determining engagement levels of an audience and providing associated recommendations to a presenter, in accordance with embodiments of the present invention.

FIG. 2 is a flowchart depicting operational steps of engagement level program 200, a program for determining engagement levels of an audience and providing associated recommendations to a presenter, in accordance with embodiments of the present invention. In one embodiment, engagement level program 200 can initiate at the start of a presentation. In another embodiment, engagement level program 200 can initiate in response to a request from a user (e.g., from a presenter utilizing computing device 150). In a further embodiment, engagement level program 200 can initiate at defined moments in time (e.g., at the start of a class or presentation, every 5 minutes, at defined points during a presentation or class, etc.). In other embodiments, engagement level program 200 can run as a background process on server 140, while analyzing sensor data during a presentation.

In step 202, engagement level program 200 receives sensor data. In one embodiment, engagement level program 200 receives sensor data from one or more of sensors 110, sensors 120, and sensors 130. In example embodiments, sensors 110, sensors 120, and sensors 130 are each communicatively connected to server 140 (e.g., via network 105) and can concurrently provide a stream of sensor data to server 140. In another example embodiment, engagement level program 200 can retrieve sensor data from one or more of sensors 110, sensors 120, and sensors 130, in response to a request for real-time sensor data from a presenter. In an additional example embodiment, server 140 can execute multiple instances of engagement level program 200, with respective instances associated with a corresponding instance of sensors 110, sensors 120, and sensors 130.

In various embodiments, engagement level program 200 receives sensor data from sensors 110, sensors 120, and sensors 130, and engagement level program 200 can determine which instance of sensors the received data is sent from. In addition, based on the location of the respective sensor, and data in user data 1456, engagement level program 200 can determine which user that corresponds to the received sensor data. In another embodiment, engagement level program 200 can gather sensor data as a periodic snapshot of the current sensor state, or additionally, as a vector of sensor states over a period of time. For example, at predefined intervals during a lesson during a lesson, engagement level program 200 receives sensor data from sensors in the audience (e.g., sensors 110, sensors 120, sensors 130) that correspond to multiple audience members, such as students.

As discussed in further detail above with regard to FIG. 1, sensors 110, sensors 120, and sensors 130 can include a device that is a combination of the capacitive touch sensors and the accelerometers, along with a wireless communication module, embedded and/or mounted onto desk and chair surfaces. The accelerometers can operate to detect movements of a chair and/or desk, such as tapping on the desk, tapping a foot (which transfers oscillatory motion to the chair), tilting of the chair, etc. The capacitive sensors can operate similar to smartphone screen sensors. For example, the capacitive sensors can comprise a grid of wires meeting near a small air gap, which creates a field. When an individual touches the field (e.g., one centimeter or close proximity to the wires), the capacitance between the wires changes, which can be detected by a programmed microcontroller, and converted into a touch map. Accordingly, engagement level program 200 receives signals of sensor data that indicates movements of audience members, and contact data to chairs and desks of audience members, in accordance with embodiments of the present invention.

In step 204, engagement level program 200 derives posture information utilizing the received sensor data. In one embodiment, engagement level program 200 analyzes the received sensor data (from step 202) utilizing posture data set 144 to determine which postures are represented in the received sensor data. As discussed above, posture data set 144 is representative of a reference data set that server 140 can utilize to determine a user posture that corresponds to received sensor data. For example, posture data set 144 includes information that maps sensor data signals (e.g., from accelerometers and capacitive sensors of sensors 110, sensors 120, and sensors 130) to corresponding postures of audience members (i.e., a mapping of a combination of sensors signals to a slouching posture, etc.). In additional embodiments, based on how closely sensor data matches information in posture data set 144, engagement level program 200 can determine a confidence level/score that corresponds to derived posture information from the sensor data.

In various embodiments, engagement level program 200 receives data signals from the sensors, and then transforms and classifies the received sensor signals into a form for comparison/analysis utilizing posture data set 144. Engagement level program 200 can then determine posture information and body language data from the classified signals utilizing the mapping data in posture data set. In example embodiments, engagement level program 200 identifies characteristics of user postures that are included in the received sensor data.

In another aspect, engagement level program 200 can determine posture information that is personalized to a particular identified user, based on utilizing user-specific data from user data 146 in combination with posture data set 144. For example, user data 146 can include historical data of characterized posture data that tailored to a particular audience member. In this example, engagement level program 200 can utilize the tailored posture data to determine posture characteristics from the sensor data with increased accuracy. In addition, engagement level program 200 can identify a unique signature model associated with a user (stored in user data 146) to utilize in the determination of posture information, and to identify the particular user that corresponds to a set of received sensor data.

In a first example scenario, engagement level program 200 receives sensor data (in step 202) from sensor 110, which corresponds to a desk and chair of a first user. Engagement level program 200 utilizes posture data set 144 to analyze the received sensor data. In addition, engagement level program 200 can also utilize information in user data 146 that is associated with the first user when analyzing the received sensor data. In this example scenario, engagement level program 200 determines that the received sensor data matches information in posture data 146 that indicates a posture of the first user slouching in the chair (based on capacitance sensor signals) and the first user is tapping a foot on the ground (based on accelerometer signals). Accordingly, engagement level program 200 determines posture information corresponding to the first user.

In a second example scenario, engagement level program 200 receives sensor data (in step 202) from sensor 120, which corresponds to a desk and chair of a second user. Engagement level program 200 utilizes posture data set 144 to analyze the received sensor data. In addition, engagement level program 200 can also utilize information in user data 146 that is associated with the second user when analyzing the received sensor data. In this example scenario, engagement level program 200 determines that the received sensor data matches information in posture data 146 that indicates a posture of the second user sitting upright in the chair with a hand on the desk making writing motions (based on capacitance sensor signals). Accordingly, engagement level program 200 determines posture information corresponding to the second user.

In step 206, engagement level program 200 determines an engagement level for a user based on the derived posture information. In one embodiment, engagement level program 200 determines whether the posture information (derived in step 204) corresponds to an engaged user, or a disengaged user. In example embodiments, engagement level program 200 correlates the determined posture information (from step 206) to indications of engagement level data in storage device 142 (e.g., in posture data set 144 and user data 146). In additional embodiments, based on how closely posture information correlates with a defined engagement level (e.g., a yes/no definition of engagement), engagement level program 200 can determine a confidence level/score that corresponds to determined engagement level.

In further embodiments, engagement level program 200 can also determine and utilize contextual information as factors in determining an engagement level. For example, contextual data can include a presentation topic, temperature and humidity of the presentation area, duration of the presentation, historical engagement data (e.g., corresponding to a specific user, specific presentation, etc.). Engagement level program 200 can leverage the determined contextual data as additional factors in the process of determining engagement levels, and corresponding recommendations for improving engagement.

Engagement level program 200 can utilize user-specific engagement level information in user data 146 to determine an engagement level that is tailored to a particular user and corresponding context. For example, user data 146 stores user-specific mappings of particular postures to corresponding engagement level information (e.g., posture indicating device usage mapped to not engaged) and mappings of contextual data to engagement level information (e.g., high humidity and long presentation mapped to not engaged). In additional embodiments, engagement level program 200 can infer a learning context from historical knowledge of an audience member (e.g., historical knowledge model of a learner in a classroom), through determining and learning engagement outcomes based on corresponding content, topics, subjects, etc.

In one embodiment, engagement level program 200 determined respective engagement levels for each identified audience member based on respective posture information. In another embodiment, engagement level program 200 determines a cumulative engagement level for the entire audience utilizing aggregated posture information for the audience. In various embodiments, engagement level program 200 can correlate the determined posture information (from step 204) to a yes/no indication of whether a user is engaged or not engaged. In another embodiment, engagement level program 200 can correlate the determined posture information to an engagement score (e.g., on a scale of 1 to 5, with 1 being least engaged and 5 being most engaged).

In the previously discussed first example scenario, engagement level program 200 determined that the received sensor data (from step 202) matches information in posture data 146 that indicates a posture of the first user slouching in the chair (based on capacitance sensor signals) and the first user is tapping a foot on the ground (based on accelerometer signals). In this example scenario, engagement level program 200 determines that the posture information of the first user slouching in the chair and foot tapping maps to an engagement level of not engaged. Accordingly, engagement level program 200 determines that the engagement level for the first user is "not engaged."

In the previously discussed second example scenario, engagement level program 200 determined that the received sensor data matches information in posture data 146 that indicates a posture of the second user sitting upright in the chair with a hand on the desk making writing motions (based on capacitance sensor signals). In this example scenario, engagement level program 200 determines that the posture information of the second user sitting upright in the chair with a hand on the desk making writing motions maps to an engagement level of engaged. Accordingly, engagement level program 200 determines that the engagement level for the second user is "engaged."

In decision step 208, engagement level program 200 determines whether an engagement level indicates that a user is not engaged. In one embodiment, engagement level program 200 compares the determined engagement level to a threshold value that defines a minimum level of engagement. In additional aspects, engagement level program 200 can utilize a confidence level associated with a determined engagement level in determining whether a user meets a minimum level of engagement. For example, engagement level program 200 can also utilize a confidence level threshold indicating whether to utilize a determined engagement level or return (to step 202) to gather updates sensor data.

In one embodiment, engagement level program 200 can utilize a common threshold for the audience members. In another embodiment, engagement level program 200 can utilize user-specific engagement level thresholds, based on information in user data 146. In further embodiments, engagement level program 200 stores the derived posture information (from step 204), the determinized engagement level (from step 206), and associated contextual information in user data 146, associated with respective audience members.

In response to determining that the audience does not include a user that is not engaged (decision step 208, NO branch), engagement level program 200 receives updates sensor data (step 202). In an alternative embodiment, in response to determining that the audience does not include a user that is not engaged (decision step 208, NO branch), engagement level program 200 can end (and reinitiate in response to receiving updated sensor data). In other aspects, engagement level program 200 can receive updates sensor data (return to step 202) for users that are engaged (or with associated data that does not meet a minimum confidence level), and engagement level program 200 can also (concurrently) proceed (to step 210) for users that are associated with a "not engaged" engagement level (decision step 208, YES branch).

In the previously discussed first example scenario, engagement level program 200 determined that the engagement level for the first user is "not engaged." Then, in decision step 208, engagement level program 200 determines that the first user does not meet the minimum engagement threshold and is a "not engaged" user (decision step 208, YES branch). In the previously discussed second example scenario, engagement level program 200 determined that the engagement level for the second user is "engaged." Then, in decision step 208, engagement level program 200 determines that the second user does meet the minimum engagement threshold and is an "engaged" user (decision step 208, NO branch).

In step 210, engagement level program 200 determined recommendations to increase engagement. More specifically, in response to determining that an engagement level of a user indicates that the user is not engaged (decision step 208, YES branch), engagement level program 200 determines recommendations to increase engagement of the user (step 210). In one embodiment, engagement level program 200 determines recommendations of actions that a presenter can perform to increase engagement of audience members. In various embodiments, engagement level program 200 can also determine and utilize contextual data in the determinations of actions to recommend. For example, contextual data can include a presentation topic, temperature and humidity of the presentation area, duration of the presentation, historical engagement data (e.g., corresponding to a specific user, specific presentation, etc.). In an additional embodiment, engagement level program 200 can determine a recommendation of an action to increased engagement of multiple, or all, individuals in the audience.

In another embodiment, engagement level program 200 can identify information in user data 146 to utilize in determining recommendations for particular audience members (e.g., user-specific recommendations based on historical data). For example, engagement level program 200 can determine recommendations from historical information in user data 146, which indicates actions for a particular user that have been previously performed and did successfully increase engagement of the user. In a further embodiment, engagement level program 200 can determine and learn contextual information of an audience member, such as a time of day, social media context, context based on information that learners have previously learned in a class, learning goals, and other factors that can influence engagement.

In an example embodiment, engagement level program 200 determines recommendations of recommended postures (i.e., physical orientations) that increase engagement for audience members that are exhibiting an indicated low engagement levels (based on decision step 208 determination). In another example embodiment, engagement level program 200 generates recommendations of points during the presentation (or a point in time) to insert a topic or content, that is relevant to the presentation topic, which can increase audience member engagement. In additional example embodiments, engagement level program 200 can recommend that the presenter interact with the audience (or one or more particular audience members), as an action to increase engagement.

In a further example embodiment, engagement level program 200 can identify if an audience member (that is not engaged) is utilizing a device (e.g., smartphone), based on received sensor data and determined posture information (from steps 202 and 204). Engagement level program 200 can then determine a recommendation that includes addressing the usage of the device (e.g., instructing the individual to stop using the device, etc.). In an example scenario, if the device being utilized by the audience member is registered with server 140 (e.g., the audience member has registered the device, the device was provided by a school, etc.), then engagement level program 200 include a recommendation to send an action directly to the device. For example, engagement level program 200 can determine a recommended action to send a message to the device, temporarily disable the device, direct the device to relevant information, etc.

In the previously discussed first example scenario, engagement level program 200 determined that the engagement level for the first user is "not engaged." Engagement level program 200 can then determine a recommended action for the presenter to perform to increase the engagement level of the first user. In one example, engagement level program 200 can determine a recommendation for the presenter to initiate an interaction with the first user (e.g., pose a question to the first user, instruct first user to stop using a smartphone, etc.). In another example, engagement level program 200 can determine a recommendation that the first user change postures, and a corresponding recommended posture. In another aspect, engagement level program 200 can determine a recommendation based on data in user data 146. For example, engagement level program 200 can identify a topic of interest to the first user (in user data 146 and based on historical data) and determine a recommendation for the presenter to mention the topic of interest, to increase engagement of the user.

In step 212, engagement level program 200 sends data to the presenter. In one embodiment, engagement level program 200 sends determined recommendations (from step 210), and other associated data, to the presenter. For example, engagement level program 200 can send data to computing device 150, which is associated with the presenter. In another embodiment, engagement level program 200 can send data to other defined users (e.g., an administrative user, etc.). In an example embodiment, engagement level program 200 identifies a highest scoring recommendation (e.g., for a particular audience member) and sends the highest scoring recommendation to the presenter.

In various embodiments, engagement level program 200 aggregates the gathered data for audience members and can display the aggregated data to the presenter in real-time (e.g., via computing device 150). For example, engagement level program 200 can send data indicating a number of engaged and not engaged audience members or data that indicates particular not engaged audience members, as well as identifying areas of the classroom that have higher levels of not engage users. In an additional example, engagement level program 200 aggregates engagement information for the entire audience of a presentation. In this example, engagement level program 200 sends an overall engagement level (e.g., as a score or percentage) of the audience to the presenter. In addition, engagement level program 200 can also send a highest scoring recommendation for re-engaging the audience, if necessary.

In step 214, engagement level program 200 stores results of performed actions. In one embodiment, engagement level program 200 can receive data from the presenter (e.g., via computing device 150) that indicates whether recommended actions were successful or unsuccessful, and a corresponding audience member. In various embodiments, engagement level program 200 stores the results in user data 146, associated with corresponding audience member(s). For example, engagement level program 200 receives information from the presenter indicating whether a recommended action (provided to the presenter in step 212) improved engagement of the first user. In this example, engagement level program 200 updates user data 146 associated with the first user with an indication of whether the particular recommended action increased engagement or did not increase engagement. In another embodiment, server 140 can utilize derived and stored information to generate a new, or update an existing, unique signature models that correspond to individual audience members, in accordance with various embodiments of the present invention.

In decision step 216, engagement level program 200 determines whether the presentation is complete. In various embodiments, engagement level program 200 determines whether the content being presented to the audience (e.g., lesson, video, presentation, or other form of content) has finished. For example, engagement level program 200 can determine whether the presenter (or another user) provides an indication that the presentation is complete. In another example, engagement level program 200 determines whether the presentation is complete based on a defined time (e.g., a class or presentation ends at a defined time, user-specified time, etc.).

In response to determining that the presentation is complete (decision step 216, YES branch), engagement level program 200 ends. In response to determining that the presentation is not complete (decision step 216, NO branch), engagement level program 200 receives an updated set of sensor data (return to step 202).

Figure 3:
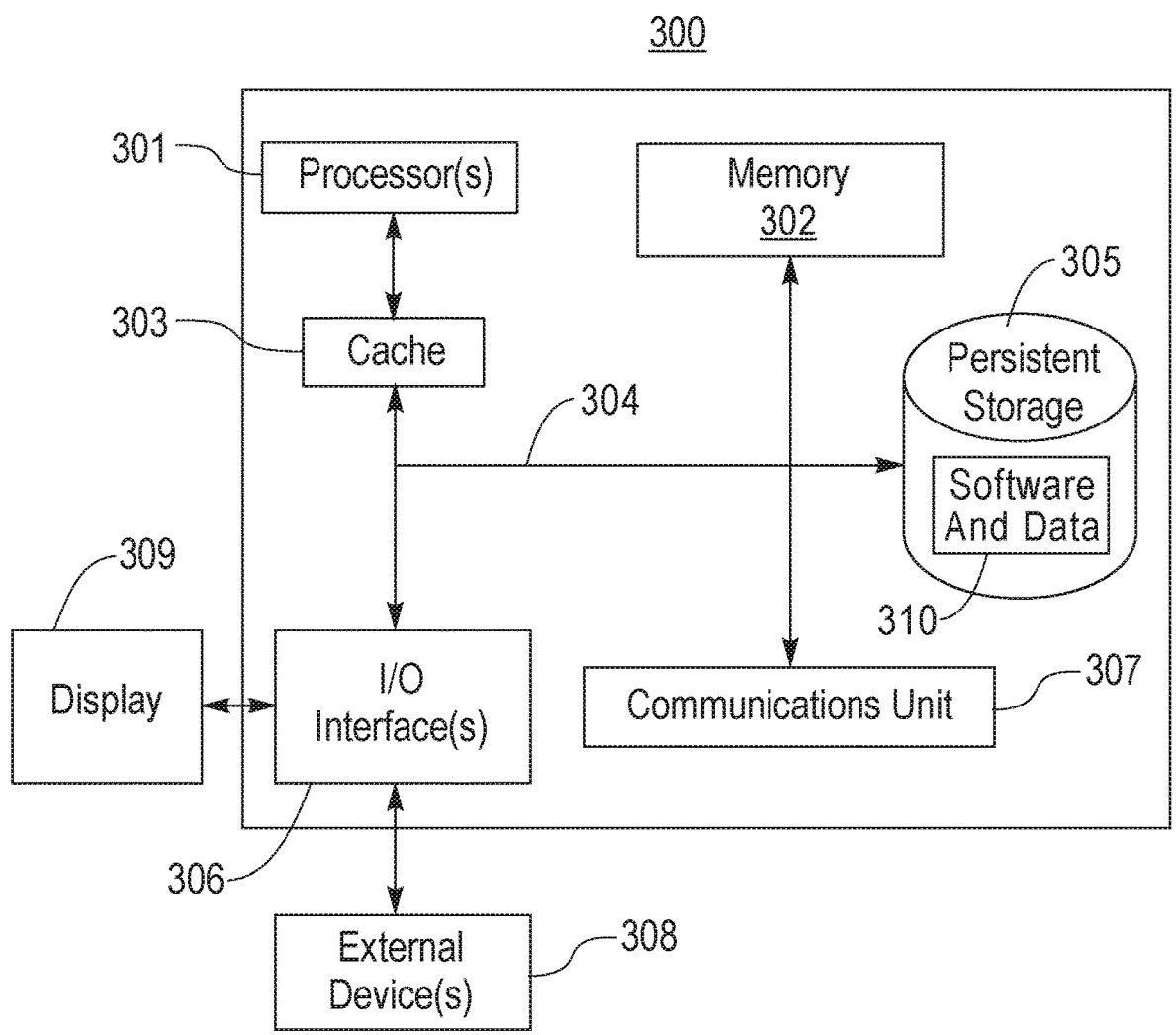
FIG. 3 depicts a block diagram of components of a computing system representative of the computing device and server of FIG. 1, in accordance with an embodiment of the present invention.

FIG. 3 depicts computer system 300, which is representative of server 140 and computing device 150, in accordance with an illustrative embodiment of the present invention. It should be appreciated that FIG. 3 provides only an illustration of one implementation and does not imply any limitations with regard to the environments in which different embodiments may be implemented. Computer system 300 includes processor(s) 301, cache 303, memory 302, persistent storage 305, communications unit 307, input/output (I/O) interface(s) 306, and communications fabric 304. Communications fabric 304 provides communications between cache 303, memory 302, persistent storage 305, communications unit 307, and input/output (I/O) interface(s) 306. Communications fabric 304 can be implemented with any architecture designed for passing data and/or control information between processors (such as microprocessors, communications and network processors, etc.), system memory, peripheral devices, and any other hardware components within a system. For example, communications fabric 304 can be implemented with one or more buses or a crossbar switch.

Memory 302 and persistent storage 305 are computer readable storage media. In this embodiment, memory 302 includes random access memory (RAM). In general, memory 302 can include any suitable volatile or non-volatile computer readable storage media. Cache 303 is a fast memory that enhances the performance of processor(s) 301 by holding recently accessed data, and data near recently accessed data, from memory 302.

Program instructions and data (e.g., software and data 310) used to practice embodiments of the present invention may be stored in persistent storage 305 and in memory 302 for execution by one or more of the respective processor(s) 301 via cache 303. In an embodiment, persistent storage 305 includes a magnetic hard disk drive. Alternatively, or in addition to a magnetic hard disk drive, persistent storage 305 can include a solid state hard drive, a semiconductor storage device, a read-only memory (ROM), an erasable programmable read-only memory (EPROM), a flash memory, or any other computer readable storage media that is capable of storing program instructions or digital information.

The media used by persistent storage 305 may also be removable. For example, a removable hard drive may be used for persistent storage 305. Other examples include optical and magnetic disks, thumb drives, and smart cards that are inserted into a drive for transfer onto another computer readable storage medium that is also part of persistent storage 305. Software and data 310 can be stored in persistent storage 305 for access and/or execution by one or more of the respective processor(s) 301 via cache 303. With respect to server 149, software and data 410 includes engagement level program 200, storage device 142, posture data set 144, and user data 146. With respect to computing device 150, software and data 410 includes user interface 152 and application 154.

Communications unit 307, in these examples, provides for communications with other data processing systems or devices. In these examples, communications unit 307 includes one or more network interface cards. Communications unit 307 may provide communications through the use of either or both physical and wireless communications links. Program instructions and data (e.g., software and data 310) used to practice embodiments of the present invention may be downloaded to persistent storage 305 through communications unit 307.

I/O interface(s) 306 allows for input and output of data with other devices that may be connected to each computer system. For example, I/O interface(s) 306 may provide a connection to external device(s) 308, such as a keyboard, a keypad, a touch screen, and/or some other suitable input device. External device(s) 308 can also include portable computer readable storage media, such as, for example, thumb drives, portable optical or magnetic disks, and memory cards. Program instructions and data (e.g., software and data 310) used to practice embodiments of the present invention can be stored on such portable computer readable storage media and can be loaded onto persistent storage 305 via I/O interface(s) 306. I/O interface(s) 306 also connect to display 309.

Display 309 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method comprising:
    receiving, by one or more processors, sensor data from a plurality of sensors located in an audience area during a presentation;
    determining, by one or more processors, an engagement level for a first individual in the audience area utilizing sensor data from sensors associated with the first individual;
    determining, by one or more processors, whether the determined engagement level for the first individual indicates that the first individual is not engaged with the presentation; and
    in response to determining that the determined engagement level of the first individual indicates that the first individual is not engaged with the presentation, determining, by one or more processors, one or more recommendations to increase engagement of the first individual,
    wherein the one or more recommendation is to temporarily disable a device associated with the first individual.

2. The method of claim 1, wherein the sensors located in the audience area include accelerometers, and wherein the sensor data from the accelerometers includes movement data of audience members within respective desks and chairs of the audience area.

3. The method of claim 1, wherein the sensors located in the audience area include capacitive sensors, wherein the sensor data from the capacitive sensors includes a touch map of audience members within respective desks and chairs of the audience area.

4. The method of claim 1, wherein determining an engagement level for a first individual in the audience area utilizing sensor data from sensors associated with the first individual further comprises:
    determining, by one or more processors, posture information corresponding to the first individual based on the received sensor data; and
    determining, by one or more processors, the engagement level for the first individual based on the determined posture information of the first individual.

5. The method of claim 4, wherein determining the engagement level for the first individual based on the determined posture information of the first individual further comprises:
    determining, by one or more processors, the engagement level for the first individual based on correlating the determined posture information for the first individual to data in a posture data set, wherein the posture data set includes mapped relationships between posture information and engagement levels.

6. The method of claim 1, further comprising:
sending, by one or more processors, the determined one or more recommendations and aggregated data associated with engagement of the audience to a presenter.

7. The method of claim 1, wherein the determining one or more recommendations are based on historical data associated with the first individual.

8. A computer program product comprising:
one or more computer readable storage media and program instructions stored on the one or more computer readable storage media, the program instructions comprising:
program instructions to receive sensor data from a plurality of sensors located in an audience area during a presentation;
program instructions to determine an engagement level for a first individual in the audience area utilizing sensor data from sensors associated with the first individual;
program instructions to determine whether the determined engagement level for the first individual indicates that the first individual is not engaged with the presentation; and
in response to determining that the determined engagement level of the first individual indicates that the first individual is not engaged with the presentation, program instructions to determine one or more recommendations to increase engagement of the first individual, wherein the one or more recommendation is to temporarily disable a device associated with the first individual.

9. The computer program product of claim 8, wherein the sensors located in the audience area include accelerometers, and wherein the sensor data from the accelerometers includes movement data of audience members within respective desks and chairs of the audience area.

10. The computer program product of claim 8, wherein the sensors located in the audience area include capacitive sensors, wherein the sensor data from the capacitive sensors includes a touch map of audience members within respective desks and chairs of the audience area.

11. The computer program product of claim 8, wherein program instructions to determine an engagement level for a first individual in the audience further comprises program instructions to:
determine posture information corresponding to the first individual based on the received sensor data; and
determine the engagement level for the first individual based on the determined posture information of the first individual.

12. The computer program product of claim 11, wherein the program instructions to determine the engagement level for the first individual based on the determined posture information of the first individual further comprises program instructions to:
determine the engagement level for the first individual based on correlating the determined posture information for the first individual to data in a posture data set, wherein the posture data set includes mapped relationships between posture information and engagement levels.

13. The computer program product of claim 8, further comprising program instructions, stored on the one or more computer readable storage media, to:
send the determined one or more recommendations and aggregated data associated with engagement of the audience to a presenter.

14. A computer system comprising:
one or more computer processors;
one or more computer readable storage media; and
program instructions stored on the computer readable storage media for execution by at least one of the one or more processors, the program instructions comprising:
program instructions to receive sensor data from a plurality of sensors located in an audience area during a presentation;
program instructions to determine an engagement level for a first individual in the audience area utilizing sensor data from sensors associated with the first individual;
program instructions to determine whether the determined engagement level for the first individual indicates that the first individual is not engaged with the presentation; and
in response to determining that the determined engagement level of the first individual indicates that the first individual is not engaged with the presentation, program instructions to determine one or more recommendations to increase engagement of the first individual, wherein the one or more recommendation is to temporarily disable a device associated with the first individual.

15. The computer system of claim 14, wherein the sensors located in the audience area include accelerometers, and wherein the sensor data from the accelerometers includes movement data of audience members within respective desks and chairs of the audience area.

16. The computer system of claim 14, wherein the sensors located in the audience area include capacitive sensors, wherein the sensor data from the capacitive sensors includes a touch map of audience members within respective desks and chairs of the audience area.

17. The computer system of claim 14, wherein program instructions to determine an engagement level for a first individual in the audience further comprises program instructions to:
determine posture information corresponding to the first individual based on the received sensor data; and
determine the engagement level for the first individual based on the determined posture information of the first individual.

18. The computer system of claim 17, wherein the program instructions to determine the engagement level for the first individual based on the determined posture information of the first individual further comprises program instructions to:
determine the engagement level for the first individual based on correlating the determined posture information for the first individual to data in a posture data set, wherein the posture data set includes mapped relationships between posture information and engagement levels.

19. The computer system of claim 14, further comprising program instructions, stored on the computer readable storage media for execution by at least one of the one or more processors, to:
send the determined one or more recommendations and aggregated data associated with engagement of the audience to a presenter.

20. The computer system of claim 14, wherein the determining one or more recommendations are based on historical data associated with the first individual.

\* \* \* \* \*